US011064988B2

(12) United States Patent
Klein et al.

(10) Patent No.: US 11,064,988 B2
(45) Date of Patent: Jul. 20, 2021

(54) IMPLANTABLE SCAFFOLD AND METHOD

(71) Applicant: LAP IQ, Inc, Los Altos, CA (US)

(72) Inventors: Michael Sigmund Klein, Salinas, CA (US); Michael George Fourkas, Sunnyvale, CA (US); James Su, Santa Clara, CA (US)

(73) Assignee: LAP IQ INC, Los Altos, CA (US)

( * ) Notice: Subject to any disclaimer, the term of this patent is extended or adjusted under 35 U.S.C. 154(b) by 438 days.

(21) Appl. No.: 16/016,604

(22) Filed: Jun. 24, 2018

(65) Prior Publication Data

US 2018/0303471 A1    Oct. 25, 2018

Related U.S. Application Data

(63) Continuation of application No. 15/256,595, filed on Sep. 4, 2016, now Pat. No. 10,166,015.

(60) Provisional application No. 62/215,715, filed on Sep. 8, 2015.

(51) Int. Cl.
*A61B 17/00* (2006.01)

(52) U.S. Cl.
CPC ...... *A61B 17/0057* (2013.01); *A61B 2017/00004* (2013.01); *A61B 2017/00623* (2013.01); *A61B 2017/00637* (2013.01); *A61B 2017/00654* (2013.01); *A61B 2017/00659* (2013.01)

(58) Field of Classification Search
CPC ...... A61B 17/0057; A61B 2017/00659; A61B 2017/00623; A61B 2017/00654; A61B 2017/00637; A61B 2017/00004
See application file for complete search history.

(56) References Cited

U.S. PATENT DOCUMENTS

| 5,342,393 | A  | * | 8/1994  | Stack ............. A61B 17/0057 24/453 |
|-----------|----|---|---------|------------------|
| 5,366,460 | A  |   | 11/1994 | Eberbach         |
| 6,120,539 | A  |   | 9/2000  | Eldridge         |
| 6,241,768 | B1 |   | 6/2001  | Agarwal          |
| 2003/0181988 | A1 | | 9/2003  | Rousseau         |
| 2006/0015142 | A1 | | 1/2006  | Malazgirt        |
| 2006/0282105 | A1 | | 12/2006 | Ford             |

OTHER PUBLICATIONS

Maurus, P.B. and Kaeding, C.C., "Bioabsorbable Implant Material Review", Oper. Tech. Sports Med 12, 158-160, 2004.

(Continued)

*Primary Examiner* — Thomas McEvoy
(74) *Attorney, Agent, or Firm* — Edell, Shapiro & Finnan, LLC

(57) ABSTRACT

A biodegradable device for maintaining the alignment of the edges of a trocar defect, consisting of two bases coupled and offset by a connector. The first base to be positioned below the defect and a second base above. The first base has a threaded hole from its upper surface but not through the lower surface. The connector attached to the bases such that there is a hole aligned with the threaded hole in the first base allowing a device to mate with the threads in the first base. The second base has a hole aligned with the hole in the connector and wide enough to allow a device to mate with the threads in the first base. The device is arranged so the distance between the lower surface of the second base and upper surface of the first base holds the fascia around the trocar defect.

3 Claims, 8 Drawing Sheets

(56) References Cited

OTHER PUBLICATIONS

Middleton, J. and Tipton A. "Synthetic Biodegradable Polymers As Medical Devices" Medical Plastics and Biomaterials Magazine, Mar. 1998.

Gilding, D.K. and Reed, A.M. "Biodegradable Polymers for Use in Surgery," Polymer, 20, 1459-1464 (Dec. 1979).

"Plastic That Comes Alive: Biodegradable plastic scaffolds support living cells in three dimensional matrices so they can grow together into tissues and even whole organs" by Astete, C.E. and Sabliov, C.M., "Synthesis and Characterization of PLGA Nanoparticles", Journal of Biomaterials Science Polymer Edition 17 (3) 247-289 (2006).

\* cited by examiner

IMPLANTABLE SCAFFOLD AND METHOD

This application is a divisional of application Ser. No. 15/256,595, filed on Sep. 4, 2016, now U.S. Pat. No. 10,166,015, issued on Jan. 1, 2019, which in turn claims benefit to Provisional Patent Application Ser. No. 62/215,715, filed on Sep. 8, 2015.

BACKGROUND OF THE INVENTION

Field of the Invention

The present invention generally relates to a wound closure device that is used either directly by a surgical team or indirectly as an attachment to a robotics controller to repair the defect typically left in the fascia layer or other tissue during laparoscopic surgery by an instrument called a trocar.

Laparoscopic surgery was introduced as an alternative to open surgical methods. Also referred to as minimally invasive surgery, the technique allows for small incision access to the intra-abdominal cavity. The approach utilizes specialized equipment such as robotics for the purposes of inflating the abdominal cavity with gas, deploying and exchanging instruments during the operation, and real time imaging with a videoscopic camera.

A laparoscopic trocar is a surgical device used for laparoscopic procedures to pierce and access the wall of an anatomical cavity, thereby forming a passageway providing communication with the inside of the cavity. Other medical instruments such as videoscopes and operating instruments can thereafter be inserted through the passageway to perform various medical procedures within the anatomical cavity.

When the procedures are over, the laparoscopic trocars are removed, leaving residual defects in the fascia-peritoneal layer. Laparoscopic trocars are typically 5-15 mm in diameter. The risk of herniation increases as the trocar size increases, and it is generally recommended that any port size larger than 5 mm should be closed because of the risk of hernias. The defect is located deep in the abdominal wall, making it difficult for the surgeon to view and repair.

Trocar site herniation is a recognized complication of laparoscopic surgery. Omental, and sometimes intestinal, herniation with incarceration and obstruction has been documented in recent surgical literature, occurring at any trocar insertion site larger than 5 mm that was not sutured at operation. The need to perform fascial closure of any trocar insertion site larger than 5 mm has now been established and is routinely practiced by laparoscopic surgeons worldwide.

However, the closure of such a trocar site fascial defect using the conventional suturing technique is often technically challenging, frustrating, unreliably successful, and even sometimes dangerous due to the limited size of skin incision, the thickness of the subcutaneous fatty layer, and necessity of blind manipulation. Moreover, the suturing that involves placement of deep blind sutures using a sharp needle after the abdomen has been decompressed is a dangerous manipulation that surgeons prefer to avoid due to potential complications such as bowel puncture and injury.

A number of techniques and instruments have been proposed to facilitate closure of the fascial defect through access of a small skin incision. Most involve passing and tying a suture, in one way or another, from one side of the trocar wound defect to the other. For this purpose, either a tapered suture or a variety of straight needles through which sutures are grasped, have been used. Problems arise as both sides of the defect may not be sutured. Also, in overweight and obese patients with thick abdominal walls, reliable fascia closure is very difficult to achieve. Inadequate repair results in delayed hernia formation, typically symptomatic or incarcerated hernia. A 6% overall hernia complication rate is reported in patients undergoing bariatric procedures. Re-operation, re-hospitalization, and extended disability frequently occur in those cases.

First generation instruments as the Carter-Thomason or Riza-Ribe® contain a catch on the end of a needle assembly to permit the grasping of a free suture at the edge of a fascial defect. Carter Thomason II and WeckEFx contain grooves, tracks, and guides to mitigate risk of bowel injury during deployment of the needle and suture positioning. Conventional open repair techniques may also be used and are typically individualized to prevent inadvertent injury to bowel. In one scenario, the handle of a dissecting forceps may be positioned through the fascial defect to protect the bowel. However, given the tight working space, using this modified open technique is often impractical and not feasible.

Even with subtle enhancements, the needle dependent Carter-Thomason II and Weck EFx require positioning of the camera, visualization of the needles during entry into the peritoneal cavity, feeding of the graspers or suture passers with the suture loop, all of which have to be repeated for every trocar defect. These needle techniques are time and effort consuming, even in the best of hands. As more defects at various sites in the abdominal wall are to be closed after advanced laparoscopic operations, the reliance on needle-based closure techniques have become more complicated and tedious.

Conventional suturing of the trocar port defect involves much traumatic manipulation including pushing, pulling and retraction of the wound, and insertion and extraction of needles. With manipulation and handling of the wound, tissue inflammation and risk of ensuing infection rise considerably. Patients are subject to pain and complications at their trocar sides in the postoperative period. The tissue edema, seroma, and hematoma formation predispose to dehiscence and hernia formation on a long-term basis.

Tedious intra-corporeal suturing techniques can be used to close trocar port defects under direct vision from within the abdominal cavity, but this is rarely done. Instead, most trocar ports are closed from the outside with the abdominal wall in a flattened configuration. As a result, the residual defect within the fascial layer is poorly visualized by the surgeon.

No matter which suturing technique or needle is used, it is not possible to eliminate the trocar site hernias completely. As described in Malazgirt (US Patent Application, pub #20060015142 published Jan. 19, 2006), the current incidence is reportedly between 0.77-3%. As complex laparoscopic surgery becomes more common, the incidence of this complication increases. The reported rates of hernia show that there is not yet any superior method in the safe closure of the trocar fascial defect.

Eldridge and Titone (U.S. Pat. No. 6,120,539 Issued Sep. 19, 2000) proposed a prosthetic repair fabric constructed from a combination of non-absorbable tissue-infiltratable fabric which faces the anterior surface of the fascia and an adhesion-resistant barrier which faces outward from the fascia. This prosthetic requires the use of sutures to hold it in place.

Eberbach (U.S. Pat. No. 5,366,460 Issued Nov. 22, 1994) proposed the use of a non-biodegradable fabric-coated loop inserted through the defect into the fascia wall, pressing against the posterior fascia wall from the intra-abdominal pressure.

Agarwal et al (U.S. Pat. No. 6,241,768 Issued Jun. 5, 2001) proposed a prosthetic device made of a biocompatible non-biodegradable mesh, which sits across the fascia defect using the abdominal pressure to hold it in place.

Rousseau (Pat Pub#20030181988) proposed a plug made of biocompatible non-biodegradable material which covers the anterior side of the fascia, the defect, as well as the posterior side of the fascia.

Malazgirt (Pat Pub#20060015142) proposed a plug/mesh non-biodegradable combination for repair of large trocar wounds. It is stated that it requires at least a "clean flat area around with a radius of 2.5 cm", and requires staples to hold it in place.

Ford and Torres (Pat Pub#20060282105) proposed a patch with a tether or strap, all made of non-biodegradable biocompatible material placed against the anterior wall of the fascia defect.

Current needle-facilitated closure techniques require that the repair of the trocar defect be performed while the trocar is still in place for the entire closure procedure. If the trocar is completely removed prior to insertion of the device it is difficult to visualize the residual defect, especially if the trocar is small. Accessing the wound post-trocar removal would make it difficult to find the residual defect, with a risk of not being able to reliably or anatomically close the defect.

What is needed is a device for assisting the healing of a trocar wound and method which enables the initial insertion of the device while the trocar is in place, but allows the completion of insertion of the device after trocar removal.

SUMMARY

A biodegradable device for maintaining the alignment of the edges of a trocar defect, consisting of two bases coupled and offset by a connector. The first base to be positioned below the defect and a second base above. The first base has a threaded hole from its upper surface but not through the lower surface. The connector attached to the bases such that there is a hole aligned with the threaded hole in the first base allowing a device to mate with the threads in the first base. The second base has a hole aligned with the hole in the connector and wide enough to allow a device to mate with the threads in the first base. The device is arranged so the distance between the lower surface of the second base and upper surface of the first base holds the fascia around the trocar defect.

DETAILED DESCRIPTION OF PREFERRED EMBODIMENTS

The potential for dislocation of tissue layers is minimized by using the inserted trocar to facilitate the initial placement of the repairing device, and then complete the repair task after the trocar is removed. However, removal of the trocar prior to inserting the repair device has the advantage of enabling the insertion of larger devices, only limited by the dimensions of the surgical defect through which the repairing device must insert.

It is also understood that one or more embodiments of this device and associated processes can be used in other surgical procedures which utilize a laparoscopic procedure going through tissue other than the fascia such as the diaphragm.

Figure 1:
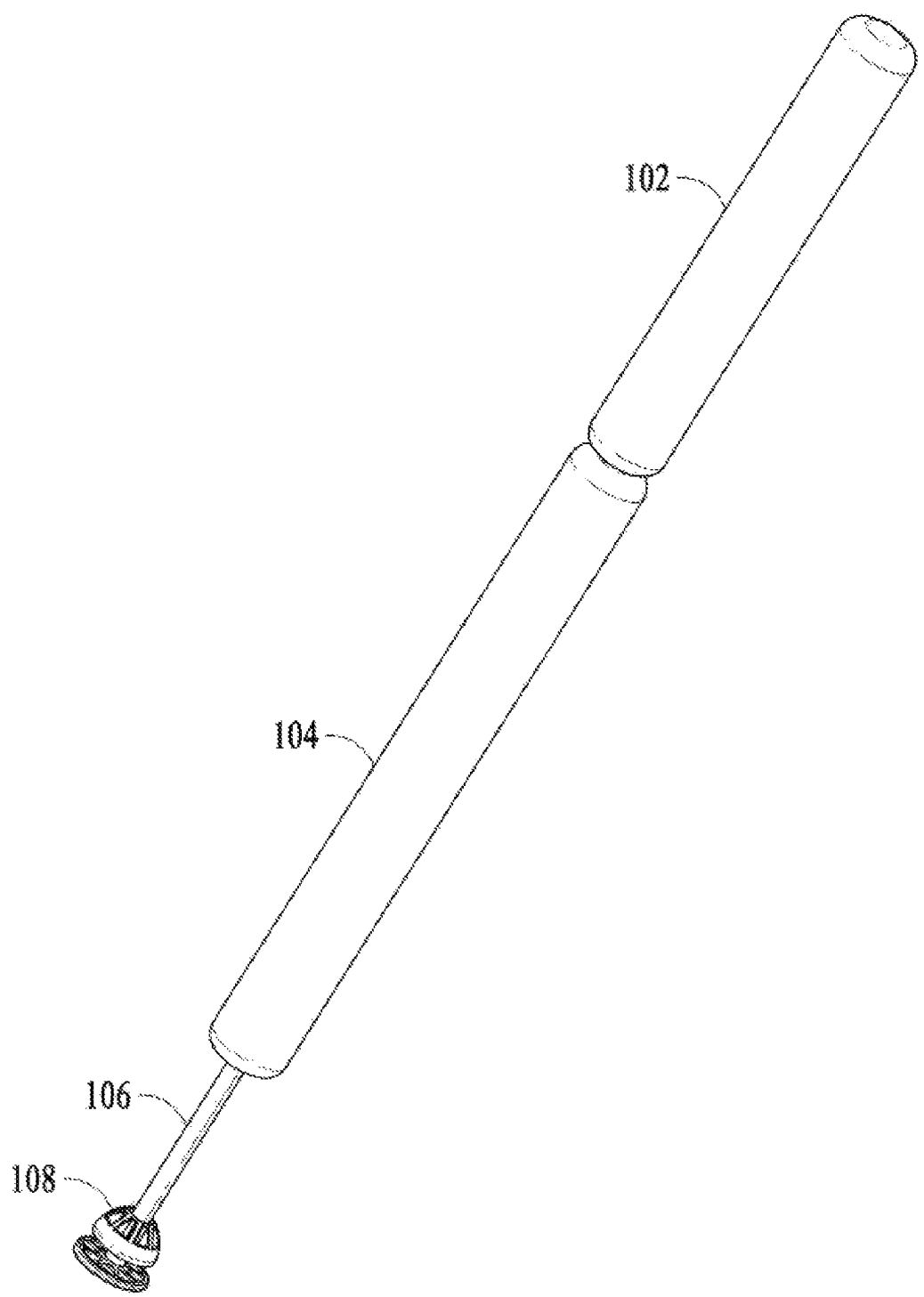
FIG. 1 shows the system including the applicator and scaffolding as it would appear prior to deployment.

FIG. 1 shows views of one or more embodiments of the device configured to be implanted. A device consists of an inner applicator 106, outer applicator 104, and the scaffold 108. The outer applicator 104 is connected to the inner applicator 106 such that the outer applicator 104 can slide over a portion of the inner applicator 106.

In one or more embodiments the inner applicator 106 and outer applicator 104 are configured to be held by a user by handle 102 attached to the inner applicator 106 to implant and align the device. In other embodiments, the handle 102, inner applicator 106 and outer applicator 104 are configured to be coupled with a robotic device to enable a user to remotely implant the device.

Figure 2:
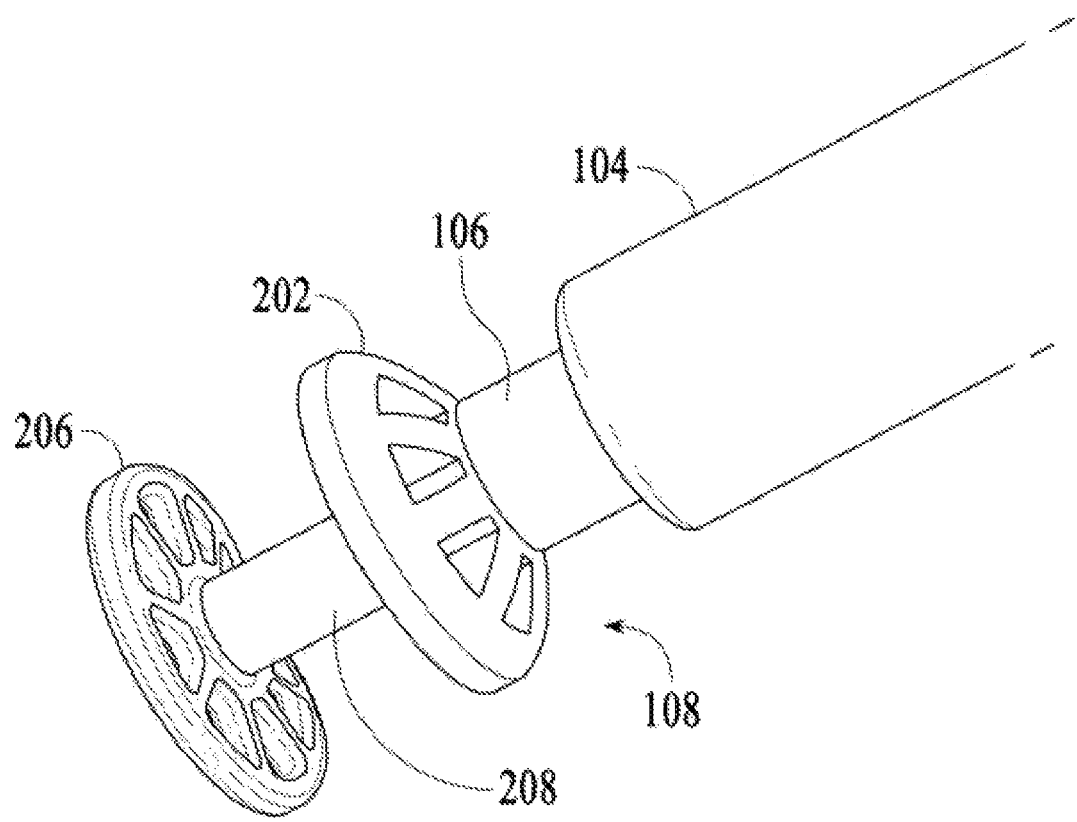
FIG. 2 shows the details of one embodiment of the coupling of the applicator to the scaffold.
Figure 3:
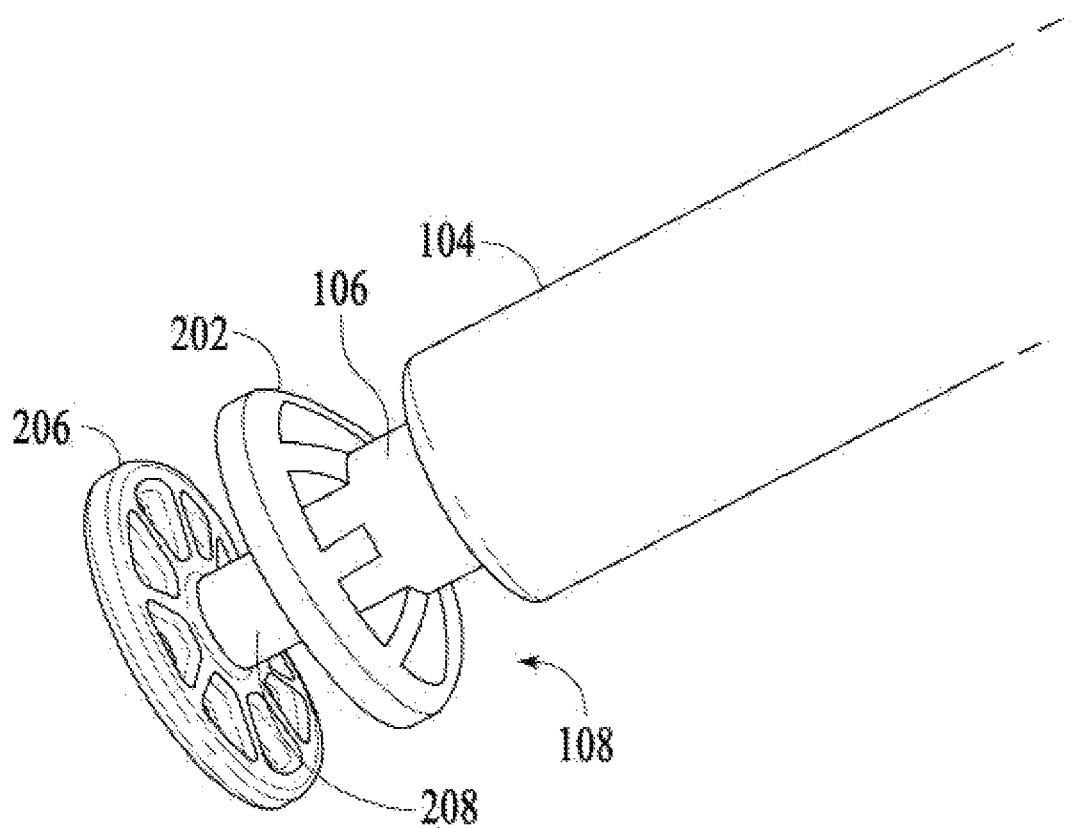
FIG. 3 shows the details of another embodiment of the coupling of the applicator to the scaffold.

FIG. 2 shows a detailed view of one or more embodiments of the scaffold 108 connected to the inner applicator 106. The inner applicator guided into place by the outer applicator 104. The inner scaffold 206 is meant to be inserted into the fascia defect and stays underneath the fascia defect once deployed. The outer scaffold 202 is meant to sit on top of the fascia defect. The coupling 208 holds the two scaffolds in place so that the tissue stays in place, the scaffolds encouraging the healing process by providing a scaffold for the tissue to grow. In one or more embodiments the coupling 208 is ribbed to enable the device to be used with various thickness of tissue around the fascia defect. The outer scaffold 202, coupling 208, and inner scaffold 206 will be collectively referred to herein as the scaffold assembly. The mechanical properties of the scaffold both maintain alignment of the fascial planes of the defect during healing and provide a mechanical barrier to herniation during healing; and until the tissue is sufficiently healed to prevent herniation.

FIG. 2 shows another embodiment of a detailed view of the coupling between the applicator and the scaffold. The outer scaffold 202 fits over the inner applicator 106 such that it can be pushed into place by the outer applicator 104. The inner applicator 106 engages the outer scaffold 202 to secure it in a retracted position during inner scaffold 206 deployment. The outer applicator 104 pushes on the outer scaffold 202 to enable engagement of the outer scaffold 202 to the inner scaffold 206, and to secure the outer scaffold 202 during detachment of the inner applicator 106 from the inner scaffold 206. In one or more embodiment, the coupling between the inner applicator 106 and outer scaffold 202 is easily removed without disrupting the scaffold assembly.

In one or more embodiments, the surfaces of the inner scaffold 206 and outer scaffold 202 have features which improve tissue engagement. In one or more embodiments, a continuous surface will maximize tissue contact and will produce uniform tissue compression. This has the disadvantage of a higher amount of polymer used, increasing cost factor. However, micron-scale porosity allows maximal cellular ingrowth and saves material by minimizing solid density. Although a non-porous surface is easier to make, the micron-scale porosity enables cellular infiltration, and macro-scale porosity has the potential of causing internal fractures in the device.

In other embodiments, the use of fenestrations on the surface of the scaffold has the potential for improving mechanical security of the device after implantation, and produces potential sites for scaffold tissue ingrowth. In other embodiments, configuring the device to minimize the effective contact area has the effect to pull tissue in and improve apposition of tissue, as well as support improved tissue healing by allowing unimpeded blood, oxygen, and nutrient supply. Fenestrations in the post may facilitate tissue ingrowth between the edges of the defect in contact on either side of the post (vs the solid construct shown).

In one of more embodiments, the outer scaffold has a convex surface facing the inner scaffold. Although a planar surface preserves the natural planar alignment of the upper inner scaffold 206 and lower outer scaffold surfaces 202, they are not in direct contact with each other. Having a convex surface is easier to deploy as it inherently pushes tissue radially outward, minimizing axial compression and relies on the tissue compression on the post. Also minimizing any retraction of the outer scaffold into the fascial layer.

In one or more embodiments, the geometry of the scaffold is lobed. In one or more embodiments, a circular geometry produces a position independent implantation, and maximizes the compression area, but has a higher polymer cost. In other embodiments, a linear geometry minimizes the polymer cost, but also minimizes the compression area. A lobed design would produce a compromise in that it is mostly position independent while lowering the polymer cost.

In one or more embodiments, the inner applicator 106 is attached to the inner scaffold 206 by a threaded connection 208 between the two.

The outer scaffold 202 sits on the superficial surface of the abdominal fascia (Scarpa fascia). It is not necessary for the scaffold assembly to cover the entire defect. Rather, it serves the purpose of stabilizing the tissue and the edges of the defect anatomically aligned and coapted to facilitate reliable wound healing.

The scaffold assembly is kept in place to hold, but not overly compress, the tissue surrounding the fascia defect to promote the healing process. In one or more embodiments, the inner scaffold 206 is diametrically larger than the outer scaffold 202. The purpose of the inner scaffold 202 is to anchor the scaffold assembly 108 to the defect, and so it must be at least wider than the width of the defect separation, and wide enough to be able to couple with the connector 208. In one or more embodiments, for 3-5 mm trocar port defects, a single piece scaffold assembly can be used because it will remove the issue of a post protrusion and is simpler to implant.

Figure 4:
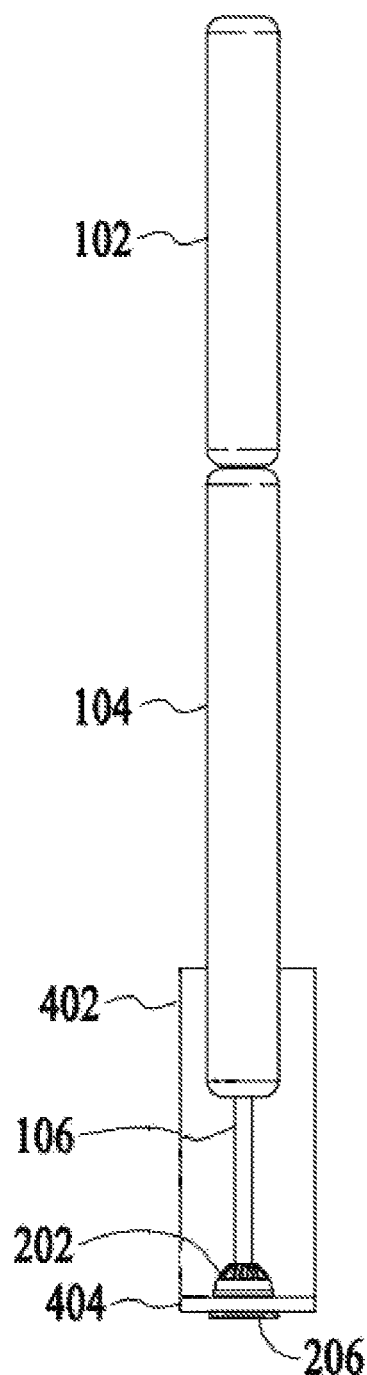
FIG. 4 shows one or more embodiments of the scaffold system at the point where the scaffolding is inserted into the abdominal cavity.

FIG. 4 shows a view of the device after the trocar has been removed and the scaffold assembly has been placed into position across the fascia 404. The outer scaffold 202 is in contact with the outer surface of the fascia 404, while the inner scaffold 206 is in contact with the peritoneal layer of the fascia 404. The inner applicator 106 is still attached to the outer scaffold 202, but is ready to be removed.

Figure 5:
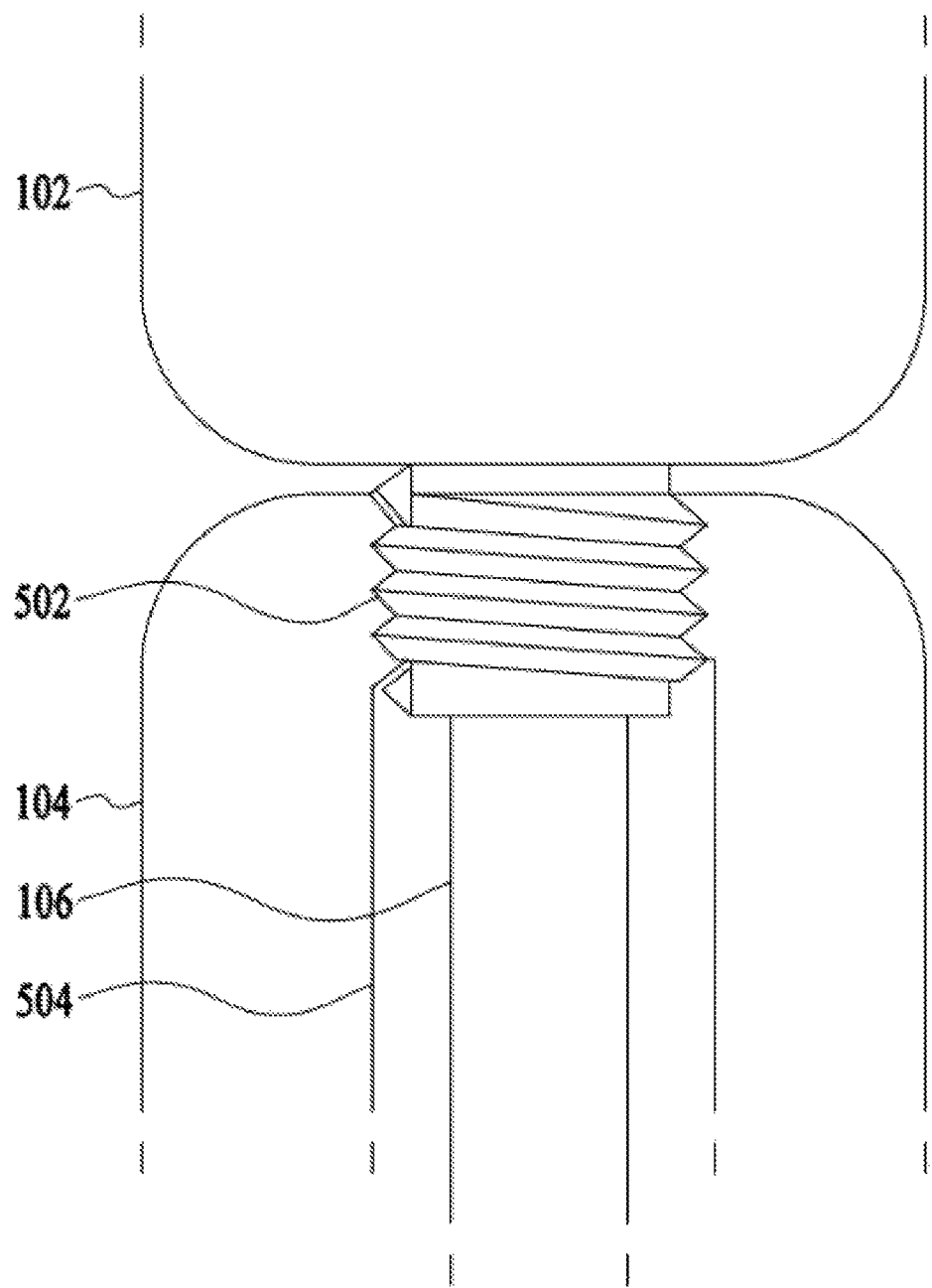
FIG. 5 shows one or more embodiments of the coupling of the inner applicator to the outer applicator.

FIG. 5 shows one or more embodiments of the coupling between the inner applicator 106, and the outer applicator 104. The inner applicator 106 is connected to the handle 102 via a threaded assembly 502. This allows one to separate the geometry of the handle 102 from that of the inner applicator 106. Also, inner diameter of the outer applicator 504 leaves a space between the inner and outer applicators inside the outer applicator 104 such that the diameter is wider than the diameter of the inner applicator 106 but smaller than the diameter of the threaded connector 502. This allows the inner applicator 106 to slide but not fall through the outer applicator 104. In one or more embodiments, the inner applicator 106 and outer applicator 104 have mating threads. During insertion they are threaded together, and this establishes the initial spacing between the inner scaffold 206 and outer scaffold 202.

Figure 6:
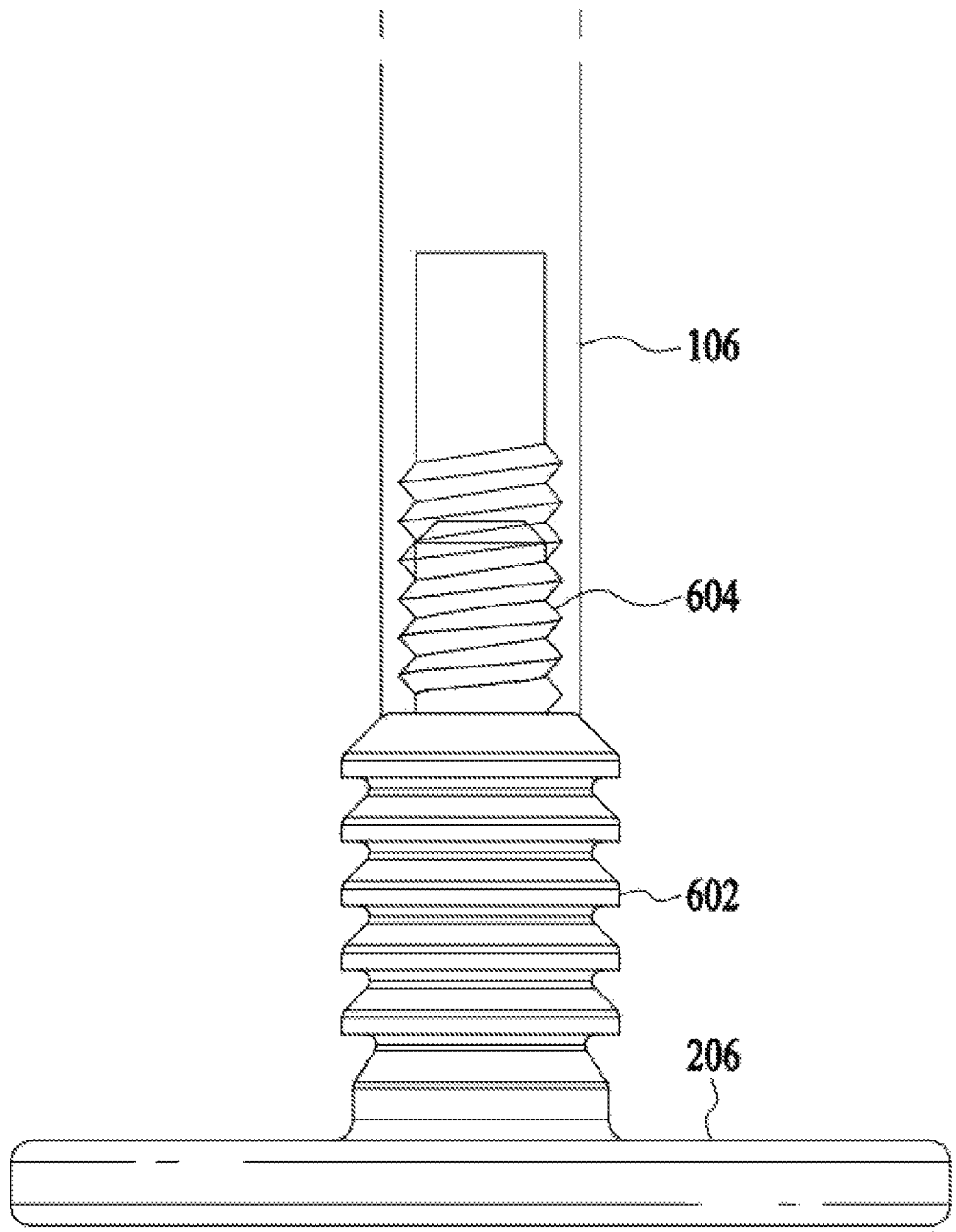
FIG. 6 shows an embodiment of the inner applicator where it is coupled to the inner scaffold.

FIG. 6 shows one or more embodiments of the coupling between inner applicator 106 and inner scaffold 206. The inner applicator 106 has a threaded cylinder in the bottom 604 that mates with a threaded barrel on top of the inner scaffold 206. There is also a barrel 602 that enables the inner scaffold 206 to connect to the outer scaffold 202.

Figure 7:
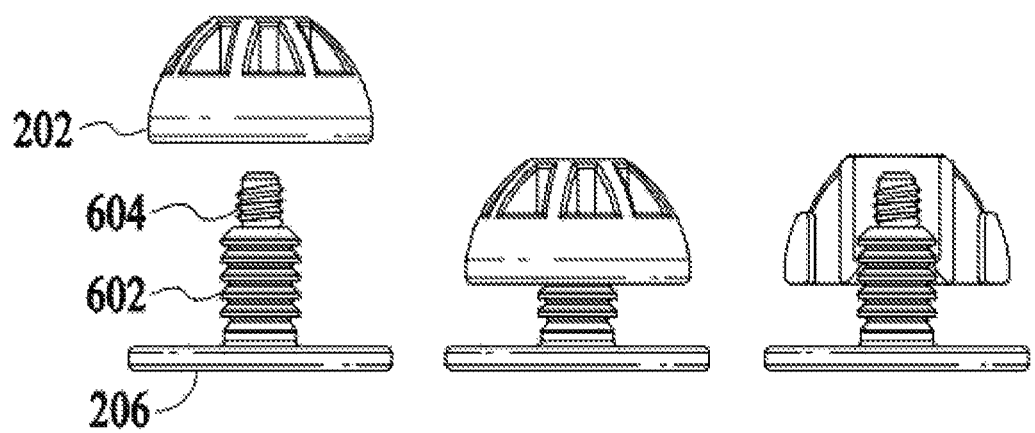
FIG. 7 shows an embodiment of the coupling of the inner to the outer scaffolding.

FIG. 7 shows one or more embodiments of how the outer scaffold and inner scaffold connect. The barrel 602 has a set of parallel ribs that mate with the inner diameter of the outer scaffold 202. This is a snap-fit rather than a screw mechanism, allowing for setting of a fixed distance between the scaffolds. The outer scaffold has a hole in the middle of the threads large enough for the inner applicator 106 to pass through. Also, the design of having the two separate parts which are joined allows one to pick and choose different inner and outer scaffold sizes, the inner scaffold 206 limited to a range between the minimum wound dimension and the trocar size, the outer scaffold 202 should be at least the size of the inner scaffold 206. The domed structure of the outer scaffold allows for scaffold to be secured together without the central post protruding from through the outer scaffold.

Figure 8:
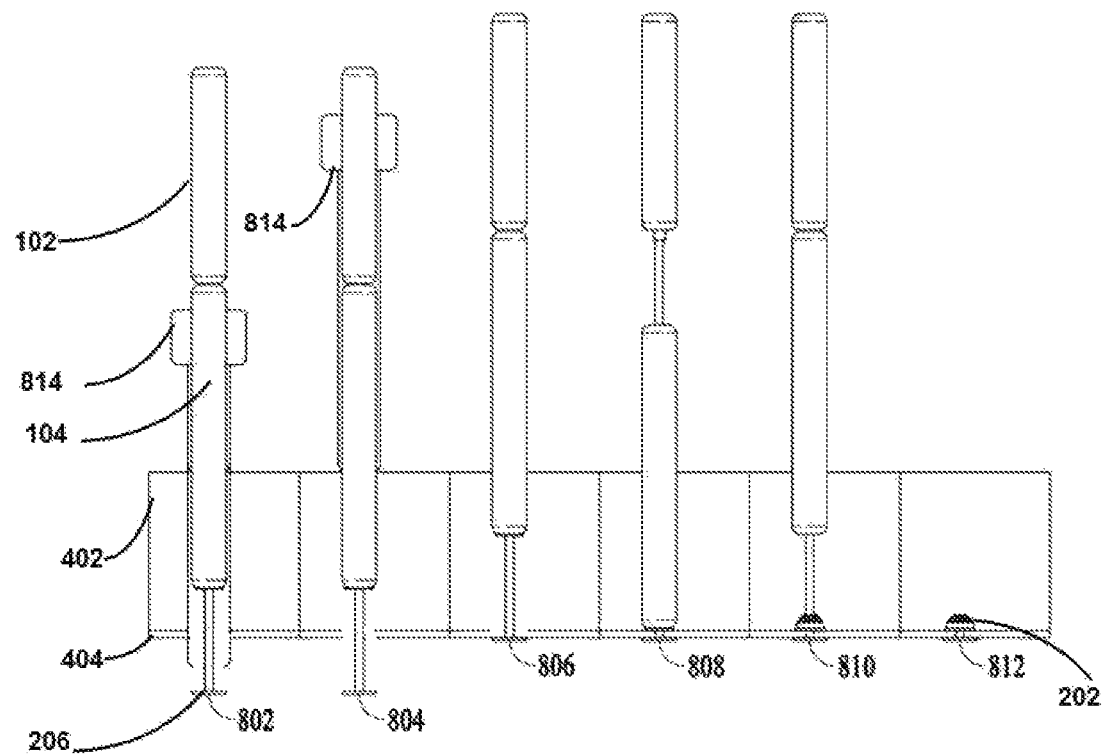
FIG. 8 shows the process of the insertion facilitated through the trocar but allowing for trocar removal before completion of the process.

FIG. 8 shows a sequence of the process of implanting the biodegradable device. First 802, the device is pushed through the fascia wall 404 with the outer scaffold 202 retracted while the trocar is still in place 814. Then 804 the trocar 814 can be removed. In one or more embodiments, this part of the procedure is done when the reversal of anesthetic muscle relaxation takes place, so that the natural tissue muscle tone surrounding the trocar defect can be used to stabilize the scaffold.

Once the trocar is removed 806, the inner scaffold 206 is pulled up using the handle 102 so that it is in contact with the inner wall of the fascia 806. Once the inner scaffold is in place, the outer applicator 104 is pushed down to place the outer scaffold 202 in place on the outer surface of the fascia 806. When ready to secure the outer scaffold 202 to the inner scaffold 206, the outer applicator 104 is first unscrewed from the inner applicator 106. The outer applicator 104 is then free to move independently and coaxially over the inner applicator 104. One can then advance the outer applicator 104 over the inner applicator 106 so that the outer scaffold 202 moves against the inner scaffold 206 until the scaffolds are fully engaged. In one or more embodiments, the scaffolds are joined by a rapid snap-fit fixation mechanism with fixed steps. In one or more embodiments, these fixed steps can be 0.1 mm, 0.25 mm, 0.5 mm, or 1 mm. Once the scaffold assembly is in place, the inner applicator 106 can be retracted and the applicators can be detached from the scaffold assembly 810. Once retracted, the handle 102 can be turned to detach the inner scaffold 206 from the outer applicator 106 and the inner applicator 104 can be turned to detach it from the outer scaffold 202, leaving the scaffold assembly in place around the fascia to hold it in place while it heals 812.

General Composition of the Wound Closure Device

Materials specified for the wound closure device are specific for its intended application and use. The scope of materials that will satisfy the requirements of this application is unusually narrow. This is a direct consequence of the specificity and functional demands characteristic of the intended surgical application.

The intention for the wound closure device is to close and secure the trocar port defect in the fascia. This requires a known and finite healing interval of some three to five months. Its purpose fulfilled at the end of this period, making continued presence of the closure device a potential liability. To prevent it from becoming a source for irritation once the healing process is completed, the implanted closure device should be removed. Consequently, to avoid the need for a second surgical intervention to remove the device, Maurus and Kaeding (Maurus, P. B. and Kaeding, C. C., "Bioabsorbable Implant Material Review", *Oper. Tech. Sports Med* 12, 158-160, 2004) found it was a primary requirement for the wound closure device to be biodegradable. This means that the materials will degrade or disintegrate, being absorbed in the surrounding tissue in the environment of the human body, after a definite, predictable and desired period of time. One advantage of such materials over non-degradable or essentially stable materials is that after the interval for which they are applied (i.e. healing time) has elapsed, they are no longer a contributing asset and do not need subsequent surgical intervention for removal, as would be required for materials more stable and permanent. This is most significant as it minimizes risks associated with repeat surgeries and the additional trauma associated with these procedures.

A disadvantage of these types of materials is that their biodegradable characteristic makes them susceptible to degradation under normal ambient conditions. There is usually sufficient moisture or humidity in the atmosphere to initiate their degradation even upon relatively brief exposure. This means that precautions must be taken throughout their processing and fabrication into useful forms, and in their storage and handling, to avoid moisture absorption. This is not a serious limitation as many materials require handling in controlled atmosphere chambers and sealed packaging; but it is essential that such precautions are observed. Middleton and Tipton (Middleton, J. and Tipton A. "Synthetic Biodegradable Polymers As Medical Devices" *Medical Plastics and Biomaterials Magazine*, March 1998) found that this characteristic also dictates that their sterilization before surgical use cannot be done using autoclaves, but alternative approaches must be employed (e.g. exposure to atmospheres of ethylene oxide or gamma radiation with cobalt 60).

While biodegradability is an essential material characteristic for the wound closure device, the intended application is such that a further requirement is that the material is formulated and manufactured with sufficient compositional and process control to provide a precisely predictable and reliable degree of biodegradability. The period of biodegradability corresponds to the healing interval for the trocar defect in the fascia layer, which is typically three to five months.

In these materials, simple chemical hydrolysis of the hydrolytically unstable backbone of the polymer is the prevailing mechanism for its degradation. As discussed in Middleton and Tipton (Middleton, J. and Tipton A referenced previously), this type of degradation when the rate at which water penetrates the material exceeds that at which the polymer is converted into water-soluble materials is known as bulk erosion.

Biodegradable polymers may be either natural or synthetic. In general, synthetic polymers offer more advantages than natural materials in that their compositions can be more readily finely-tuned to provide a wider range of properties and better lot-to-lot uniformity and, accordingly, offer more general reliability and predictability and are the preferred source.

Synthetic absorbable materials have been fabricated primarily from three polymers: polyglycolic acid (PGA), polylactic acid (PLA) and polydioxanone (PDS). These are alpha polyesters or poly (alpha-hydroxy) acids. The dominant ones are PLA and PGA and have been studied for several decades. Gilding and Reed (Gilding, D. K and Reed A. M., "Biodegradable Polymers for Use in Surgery" *Polymer* 20, 1459-1464) discussed how each of these materials has distinctive, unique properties. One of the key advantages of these polymers is that they facilitate the growth of blood vessels and cells in the polymer matrix as it degrades, so that the polymer is slowly replaced by living tissue as the polymer degrades ("Plastic That Comes Alive: Biodegradable plastic scaffolds support living cells in three dimensional matrices so they can grow together into tissues and even whole organs" by Cat Faber *Strange Horizons* http://www.strangehorizons.com/2001/20010305/plastic.shtml)

In recent years, researchers have found it desirable for obtaining specific desirable properties to prepare blends of these two dominant types, resulting in a highly useful form, or co-polymer, designated as PLGA or poly (lactic-co-glycolic acid). Asete and Sabilov (Asete, C. E. and Sabilov C. M., "Synthesis and Characterization of PLGA Nanoparticles", *Journal of Biomaterials Science—Polymer Edition* 17(3) 247-289 (2006)) discuss how this form is currently used in a host of FDA-approved therapeutic devices owing to its biodegradability and biocompatibility.

In one or more embodiments, the biodegradable wound closure device may be made of biodegradable material of different stability (i.e. half-life). While it is important for the material that is in direct contact with the fascia or lending support to that (the subfascial button base 506, screw 110, and superfascial button base 606) needs to stay in place for a few months, while the rest of the implantable structure can degrade significantly in a matter of weeks without affecting the performance of the payload. In one or more embodiments, the screw 110 would degrade sooner than the subfascial button base 506 and superfascial button base 606, so that the ends of the defect are allowed to grow together while protecting the surface of the defect.

Description of Use of One or More Embodiments of the Invention

One or more embodiments of the use of this invention are described herein. In one or more embodiments, the outer applicator is coupled to the outer scaffold first, then the inner applicator is coupled to the inner scaffold through the connector. The outer scaffold is fitted over the connector. The scaffolds, connector and applicators create what we will refer to as the applicator assembly.

The applicator assembly is inserted into the wound and the inner scaffold is pushed through the trocar defect. Once the inner scaffold is pushed through the trocar defect, the user exerts a slight upward pressure on the handle of the inner applicator to keep the inner scaffold securely against the lower fascia surface. In one or more embodiments where the outer scaffold is made to slide over the connector the user will also exert a downward pressure on the tube of the outer applicator to move the outer scaffold over the connector toward the inner scaffold until there is a positive force pushing back. In other embodiments, the tube is rotated where the outer scaffold has a threaded interface with the connector. At this point, the device is in place.

Once the device is in place, the outer applicator can be decoupled from the outer scaffold and the inner applicator is decoupled from the inner scaffold. The user is then free to close the outer wound.

Over the next few months, the wound edges will grow into each other. In one or more embodiments, the tissue may also be encouraged to grow over and/or into the device itself, where the device has a mesh in it. Over time, the device degrades and eventually dissolves into the body to be excreted without any known side effects.

What is claimed is:

1. A process for inserting a biodegradable implantable device into a trocar defect produced by a trocar placed in a fascia wall of a patient, the fascia wall comprising tissue having a thickness, the tissue have an inner surface and an outer surface, the biodegradable device having an inner scaffold, connector, and outer scaffold, the inner scaffold and outer scaffold detachably connected to an applicator and to each other, the applicator having an inner section, outer section and a handle, where the inner section is detachably connected to the inner scaffold, the outer section is detachably connected to the outer scaffold, the inner section is attached to the handle, and the inner section is slidable inside the outer section, the process comprising:

attaching the applicator to the inner and outer scaffold creating an assembly, so that the outer scaffold is on an end of the outer section and the inner scaffold is a distance away from the outer scaffold, the distance being greater than the thickness of the tissue, placing the assembly inside the trocar, pushing the assembly through the trocar defect so that the outer scaffold is above the trocar defect and the inner scaffold is below the trocar defect, removing the trocar while keeping the outer scaffold above the trocar defect and the inner scaffold below the trocar defect, pulling back on the handle so that the inner scaffold is against the inner surface of the tissue, pushing on the outer section of the applicator until the outer scaffold is against the outer surface of the tissue, detaching the outer section from the inner section, pushing down on the outer section while holding the inner section in place, until the inner scaffold is engaged with the outer scaffold by an engagement mechanism, retracting the inner section, and detaching the applicator from the scaffold assembly.

2. The process according to claim 1, wherein the engagement mechanism is a snap fit between the inner and outer scaffolds with a fixed step size.

3. The process according to claim 2, wherein the fixed step size is one of 0.1 mm, 0.25 mm, 0.5 mm and 1 mm.

* * * * *